(12) United States Patent
Bou Chedid et al.

(10) Patent No.: US 9,315,479 B2
(45) Date of Patent: Apr. 19, 2016

(54) PROCESS FOR PREPARING PYRROLIDINE

(71) Applicant: BASF SE, Ludwigshafen (DE)

(72) Inventors: Roland Bou Chedid, Mannheim (DE); Johann-Peter Melder, Böhl-Iggelheim (DE); Roman Dostalek, Neuleiningen (DE); Jörg Pastre, Bensheim (DE); Aik Meam Tan, Speyer (DE)

(73) Assignee: BASF SE, Ludwigshafen (DE)

( * ) Notice: Subject to any disclaimer, the term of this patent is extended or adjusted under 35 U.S.C. 154(b) by 265 days.

(21) Appl. No.: 13/940,964

(22) Filed: Jul. 12, 2013

(65) Prior Publication Data

US 2014/0018547 A1 Jan. 16, 2014

Related U.S. Application Data

(60) Provisional application No. 61/671,121, filed on Jul. 13, 2012.

(51) Int. Cl.
C07D 295/027 (2006.01)

(52) U.S. Cl.
CPC .................. *C07D 295/027* (2013.01)

(58) Field of Classification Search
None
See application file for complete search history.

(56) References Cited

U.S. PATENT DOCUMENTS

| | | | |
|---|---|---|---|
| 3,275,554 A | 9/1966 | Wagenaar | |
| 3,751,475 A | 8/1973 | van der Voort et al. | |
| 4,832,702 A | 5/1989 | Kummer et al. | |
| 6,187,957 B1 | 2/2001 | Meyer et al. | |
| 8,487,135 B2 * | 7/2013 | Kubanek et al. | 564/480 |
| 2003/0089591 A1 | 5/2003 | Wolfert et al. | |
| 2005/0000791 A1 | 1/2005 | Wolfert et al. | |
| 2010/0274010 A1 | 10/2010 | Kubanek et al. | |
| 2010/0274055 A1 | 10/2010 | Kubanek et al. | |
| 2011/0054167 A1 | 3/2011 | Kubanek et al. | |
| 2011/0137030 A1 | 6/2011 | Kubanek et al. | |
| 2012/0035049 A1 | 2/2012 | Kubanek et al. | |

FOREIGN PATENT DOCUMENTS

| | | |
|---|---|---|
| DE | 21 25039 A1 | 12/1971 |
| DE | 36 11 230 A1 | 10/1987 |
| DE | 19859776 A1 | 6/2000 |
| EP | 1 312 599 A1 | 5/2003 |
| EP | 1 312 600 A1 | 5/2003 |
| WO | WO-03/051508 A1 | 6/2003 |
| WO | WO-2008/006750 A1 | 1/2008 |
| WO | WO-2009080506 A1 | 7/2009 |
| WO | WO-2009080507 A1 | 7/2009 |
| WO | WO-2009080508 A1 | 7/2009 |
| WO | WO-2011067199 A1 | 6/2011 |
| WO | WO-2011157710 A1 | 12/2011 |
| WO | WO-2014/184039 A1 | 11/2014 |
| WO | WO-2014/184048 A1 | 11/2014 |

OTHER PUBLICATIONS

English Translation of International Search Report for PCT/EP2013/064321 dated Aug. 21, 2013.
U.S. Appl. No. 13/158,667, filed Jun. 13, 2011, Wigbers et al.
U.S. Appl. No. 13/273,784, filed Oct. 14, 2011, Wigbers et al.
U.S. Appl. No. 13/284,178, filed Oct. 28, 2011, Wigbers et al.
U.S. Appl. No. 13/906,960, filed May 31, 2013, Bou Chedid et al.
U.S. Appl. No. 13/906,931, filed May 31, 2013, Bou Chedid et al.
U.S. Appl. No. 13/910,602, filed Jun. 5, 2013, Bou Chedid et al.
U.S. Appl. No. 13/910,554, filed Jun. 5, 2013, Bou Chedid et al.

* cited by examiner

*Primary Examiner* — Rebecca Anderson
*Assistant Examiner* — Po-Chih Chen
(74) *Attorney, Agent, or Firm* — Drinker Biddle & Reath LLP

(57) ABSTRACT

Process for preparing pyrrolidine of the formula I

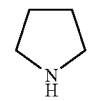

(I)

by reacting 1,4-butanediol (BDO) of the formula II

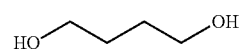

(II)

with ammonia in the presence of hydrogen and a supported, metal-containing catalyst, wherein the catalytically active mass of the catalyst, prior to its reduction with hydrogen, comprises oxygen-containing compounds of aluminum, copper, nickel and cobalt and in the range from 0.2 to 5.0% by weight of oxygen-containing compounds of tin, calculated as SnO, and the reaction is carried out in the liquid phase at an absolute pressure in the range from 160 to 220 bar, a temperature in the range from 160 to 230° C., using ammonia in a molar ratio to BDO used of from 5 to 50 and in the presence of 1.0 to 4.5% by weight of hydrogen, based on the amount of BDO used.

27 Claims, No Drawings

PROCESS FOR PREPARING PYRROLIDINE

CROSS-REFERENCE TO RELATED APPLICATIONS

This application claims benefit (under 35 U.S.C. §119(e)) of U.S. Provisional Application 61/671,121, filed Jul. 13, 2012, which is incorporated by reference herein in its entirety.

BACKGROUND OF THE INVENTION

The present invention relates to a process for preparing pyrrolidine of the formula I

(I)

by reacting 1,4-butanediol (BDO) of the formula II

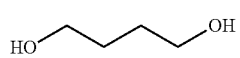

(II)

with ammonia in the presence of hydrogen and a supported, metal-containing catalyst.

Pyrrolidine is used inter alia as an intermediate and/or reagent in the production of fuel additives (U.S. Pat. No. 3,275,554 A; DE 21 25 039 A and DE 36 11 230 A), surfactants, drugs and crop protection compositions, hardeners for epoxy resins, catalysts for polyurethanes, and as an intermediate and/or reagent in the production of quaternary ammonium compounds, plasticizers, corrosion inhibitors, as synthetic resins, ion exchangers, textile auxiliaries, dyes, vulcanization accelerators and emulsifiers.

WO 03/051508 A1 (Huntsman Petrochemical Corp.) relates to processes for the amination of alcohols using specific Cu/Ni/Zr/Sn-containing catalysts which, in a further embodiment, comprise Cr instead of Zr (see page 4, lines 10-16). The catalysts described in this WO application comprise no aluminum oxide and no cobalt.

WO 2008/006750 A1 (BASF AG) relates to certain Pb, Bi, Sn, Sb and/or In-doped, zirconium dioxide-, copper-, nickel- and cobalt-containing catalysts and their use in processes for preparing an amine by reacting a primary or secondary alcohol, aldehyde and/or ketone with hydrogen and ammonia, a primary or secondary amine. Aluminum oxide supports are not taught.

WO 2009/080507 A1 (BASF SE) relates to certain Sn- and Co-doped, zirconium dioxide-, copper- and nickel-containing catalysts and their use in processes for preparing an amine by reacting a primary or secondary alcohol, aldehyde and/or ketone with hydrogen and ammonia, a primary or secondary amine. Aluminum oxide supports are not taught.

WO 2009/080506 A1 (BASF SE) describes certain Pb, Bi, Sn, Mo, Sb and/or P-doped, zirconium dioxide-, nickel- and iron-containing catalysts and their use in processes for preparing an amine by reacting a primary or secondary alcohol, aldehyde and/or ketone with hydrogen and ammonia, a primary or secondary amine. Aluminum oxide supports are not taught. Preferably, the catalysts comprise no Cu and no Co.

WO 2009/080508 A1 (BASF SE) teaches certain Pb, Bi, Sn and/or Sb-doped, zirconium dioxide-, copper-, nickel-, cobalt- and iron-containing catalysts and their use in processes for preparing an amine by reacting a primary or secondary alcohol, aldehyde and/or ketone with hydrogen and ammonia, a primary or secondary amine. Aluminum oxide supports are not taught.

WO 2011/067199 A1 (BASF SE) relates to certain aluminum oxide-, copper-, nickel-, cobalt- and tin-containing catalysts and their use in processes for preparing an amine from a primary or secondary alcohol, aldehyde and/or ketone. The preparation of pyrrolidines from 1,4-diols is mentioned in general on page 22, lines 13-15, and page 24, lines 39-42.

WO 2011/157710 A1 (BASF SE) describes the preparation of certain cyclic tertiary methylamines, where an amino alcohol from the group 1,4-aminobutanol, 1,5-aminopentanol, aminodiglycol (ADG) or aminoethyl-ethanolamine is reacted with methanol at elevated temperature in the presence of a copper-containing heterogeneous catalyst in the liquid phase.

WO 2012/049101 A1 (BASF SE) relates to a process for preparing certain cyclic tertiary amines by reacting an amino alcohol from the group 1,4-aminobutanol, 1,5-aminopentanol, aminodiglycol (ADG) or aminoethyl-ethanolamine with a certain primary or secondary alcohol at elevated temperature in the presence of a copper-containing heterogeneous catalyst in the liquid phase.

DE 198 59 776 A1 (BASF AG) relates to certain amination processes using catalyst moldings which comprise oxygen-containing compounds of titanium and of copper and metallic copper.

BRIEF SUMMARY OF THE INVENTION

The object of the present invention was to improve the economic feasibility of processes to date for preparing pyrrolidine of the formula I and to overcome one or more disadvantages of the prior art. The aim was to find conditions which can be established in technical terms in a simple manner and which make it possible to carry out the process with high conversion, high yield, space-time yield (STY), selectivity coupled with simultaneously high mechanical stability of the catalyst molding and low "runaway risk".

[Space-time yields are given in "amount of product/(catalyst volume·time)"(kg/($l_{cat.}$·h)) and/or "amount of product/(reactor volume·time)"(kg/($l_{reactor}$·h))].

A DETAILED DESCRIPTION OF THE INVENTION

Accordingly, a process for preparing pyrrolidine of the formula I

(I)

by reacting 1,4-butanediol (BDO) of the formula II

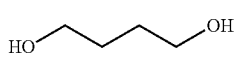

(II)

with ammonia in the presence of hydrogen and a supported, metal-containing catalyst has been found, wherein the catalytically active mass of the catalyst, prior to its reduction with hydrogen, comprises oxygen-containing compounds of aluminum, copper, nickel and cobalt and in the range from 0.2 to 5.0% by weight of oxygen-containing compounds of tin, calculated as SnO, and the reaction is carried out in the liquid phase at an absolute pressure in the range from 160 to 220 bar, a temperature in the range from 160 to 230° C., using ammonia in a molar ratio to BDO used of from 5 to 50 and in the presence of 1.0 to 4.5% by weight of hydrogen, based on the amount of BDO used.

In particular, catalysts whose catalytically active mass, prior to their reduction with hydrogen, comprises in the range from 15 to 80% by weight of oxygen-containing compounds of aluminum, calculated as $Al_2O_3$, 1 to 20% by weight of oxygen-containing compounds of copper, calculated as CuO, 5 to 35% by weight of oxygen-containing compounds of nickel, calculated as NiO, 5 to 35% by weight of oxygen-containing compounds of cobalt, calculated as CoO, and 0.2 to 5.0% by weight of oxygen-containing compounds of tin, calculated as SnO, are used in the aforementioned amination process.

The process can be carried out continuously or discontinuously. Preference is given to a continuous procedure.

In the circulating-gas mode, the starting materials (BDO, ammonia) are vaporized in a circulating-gas stream and passed to the reactor in gaseous form. The starting materials (BDO, ammonia) can also be vaporized as aqueous solutions and be supplied to the catalyst bed with the circulating-gas stream.

Preferred reactors are tubular reactors. Examples of suitable reactors with circulating-gas stream can be found in Ullmann's Encyclopedia of Industrial Chemistry, 5th Ed., Vol. B 4, pages 199-238, "Fixed-Bed Reactors".

Alternatively, the reaction takes place advantageously in a tube-bundle reactor or in a mono-stream plant. In a mono-stream plant, the tubular reactor in which the reaction takes place can consist of a serial connection of a plurality (e.g. two or three) individual tubular reactors. Optionally, an intermediate introduction of feed (comprising the BDO and/or ammonia and/or $H_2$) and/or circulating gas and/or reactor discharge from a downstream reactor is advantageously possible here. The circulating gas comprises preferably at least 10, particularly 50 to 100, very particularly 80 to 100, % by volume of $H_2$.

The circulating-gas amount is, in the case of an $H_2$ content of 80% by volume, preferably in the range from 10 to 450 m³ (stp)/[m³ of catalyst (bed volume)·h], in particular in the range from 15 to 450 m³ (stp)/[m³ of catalyst (bed volume)·h], further particularly in the range from 20 to 400 m³ (stp)/[m³ of catalyst (bed volume)·h], very particularly in the range from 25 to 400 m³ (stp)/[m³ of catalyst (bed volume)·h], e.g. 35 to 360 m³ (stp)/[m³ of catalyst (bed volume)·h].

For a different $H_2$ content, the aforementioned circulating-gas amounts change accordingly by calculation in order to keep the amount of $H_2$ (in m³ (stp)/[m³ of catalyst (bed volume)·h]) constant. [m³ (stp)=cubic meters at standard temperature and pressure=volume adjusted to standard conditions (20° C., 1 bar abs.)]. (Standard pressure=1 bar abs.).

In the process according to the invention, the catalysts are preferably used in the form of catalysts which consist only of catalytically active mass and optionally a shaping auxiliary (such as e.g. graphite or stearic acid), if the catalyst is used as moldings, i.e. comprise no further catalytically active accompanying substances.

In this connection the oxidic support material aluminum oxide ($Al_2O_3$) is deemed as belonging to the catalytically active mass.

The catalysts are used by introducing the catalytically active mass ground to powder into the reaction vessel, or by arranging the catalytically active mass after grinding, mixing with shaping auxiliaries, shaping and tempering as catalyst moldings—for example as tablets, beads, rings, extrudates (e.g. strands)—in the reactor.

The concentration data (in % by weight) of the components of the catalyst refer in each case—unless stated otherwise, to the catalytically active mass of the finished catalyst after its last heat treatment and before its reduction with hydrogen.

The catalytically active mass of the catalyst, after its last heat treatment and before its reduction with hydrogen, is defined as the sum of the masses of the catalytically active constituents and of the aforementioned catalyst support materials and comprises essentially the following constituents: aluminum oxide ($Al_2O_3$), oxygen-containing compounds of copper, nickel and cobalt and oxygen-containing compounds of tin.

The sum of the aforementioned constituents of the catalytically active mass is usually 70 to 100% by weight, preferably 80 to 100% by weight, particularly preferably 90 to 100% by weight, particularly >95% by weight, very particularly >98% by weight, in particular >99% by weight, e.g. particularly preferably 100% by weight.

The catalytically active mass of the catalysts according to the invention and used in the process according to the invention can further comprise one or more elements (oxidation state 0) or inorganic or organic compounds thereof selected from groups I A to VI A and I B to VII B and VIII of the Periodic Table of the Elements.

Examples of such elements and their compounds are:

Transition metals, such as Mn and $MnO_2$, W and tungsten oxides, Ta and tantalum oxides, Nb and niobium oxides or niobium oxalate, V and vanadium oxides and vanadyl pyrophosphate; lanthanides, such as Ce and $CeO_2$ or Pr and $Pr_2O_3$; alkaline earth metal oxides, such as SrO; alkaline earth metal carbonates, such as $MgCO_3$, $CaCO_3$ and $BaCO_3$; boron oxide ($B_2O_3$).

Preferably, the catalytically active mass of the catalysts according to the invention and used in the process according to the invention comprises no rhenium, no ruthenium, no iron and/or no zinc, in each case neither in metallic (oxidation state=0) nor in an ionic (oxidation state≠0), in particular oxidized, form.

Preferably, the catalytically active mass of the catalysts according to the invention and used in the process according to the invention comprises no silver and/or molybdenum, in each case neither in metallic (oxidation state=0) nor in an ionic (oxidation state≠0), in particular oxidized, form.

In a particularly preferred embodiment, the catalytically active mass of the catalysts according to the invention and used in the process according to the invention comprises no further catalytically active component, neither in elemental (oxidation state=0) nor in ionic (oxidation state≠0) form.

In the particularly preferred embodiment, the catalytically active mass is not doped with further metals or metal compounds.

Preferably, however, customary accompanying trace elements originating from the metal extraction of Cu, Co, Ni, Sn are excluded from this.

Preferably, the catalytically active mass of the catalyst comprises no oxygen-containing compounds of silicon and/or of zirconium.

Preferably, the catalytically active mass of the catalyst comprises no oxygen-containing compounds of titanium and/or of chromium.

The catalytically active mass of the catalyst comprises, prior to its reduction with hydrogen, in the range from 0.2 to 5.0% by weight, particularly in the range from 0.4 to 4.0% by weight, further particularly in the range from 0.6 to 3.0% by weight, further particularly preferably in the range from 0.7 to 2.5% by weight, of oxygen-containing compounds of tin, calculated as SnO.

The catalytically active mass of the catalyst comprises, prior to its reduction with hydrogen, preferably in the range from 5.0 to 35% by weight, particularly in the range from 10 to 30% by weight, further particularly in the range from 12 to 28% by weight, very particularly 15 to 25% by weight, of oxygen-containing compounds of cobalt, calculated as CoO.

Prior to its reduction with hydrogen, the catalytically active mass of the catalyst further preferably comprises in the range from 15 to 80% by weight, particularly 30 to 70% by weight, further particularly 35 to 65% by weight, of oxygen-containing compounds of aluminum, in each case calculated as $Al_2O_3$, 1 to 20% by weight, particularly 2 to 18% by weight, further particularly 5 to 15% by weight, of oxygen-containing compounds of copper, in each case calculated as CuO, and 5 to 35% by weight, particularly 10 to 30% by weight, further particularly 12 to 28% by weight, very particularly 15 to 25% by weight, of oxygen-containing compounds of nickel, in each case calculated as NiO.

The molar ratio of nickel to copper is preferably greater than 1, particularly preferably greater than 1.2, further particularly preferably in the range from 1.8 to 8.5.

The BET surface area (ISO 9277:1995) of the catalysts according to the invention and used in the process according to the invention is preferably in the range from 30 to 250 $m^2/g$, particularly in the range from 90 to 200 $m^2/g$, further particularly in the range from 130 to 190 $m^2/g$, (in each case prior to the reduction with hydrogen). These ranges are achieved in particular as a result of calcination temperatures during the catalyst preparation in the range from 400 to 600° C., particularly 420 to 550° C., (cf. below).

Various processes are possible for preparing the catalysts used in the process according to the invention. They are obtainable for example by peptization of pulverulent mixtures of the hydroxides, carbonates, oxides and/or other salts of the components with water and subsequent extrusion and tempering (heat treatment) of the resulting mass.

Preferably, precipitation methods are used for producing the catalysts according to the invention. Thus, they can be obtained for example by means of a joint precipitation of the nickel, cobalt, copper and Sn components from an aqueous salt solution comprising these elements by means of bases in the presence of a slurry of a sparingly soluble, oxygen-containing aluminum compound and subsequent washing, drying and calcination of the resulting precipitate. Sparingly soluble, oxygen-containing aluminum compounds which can be used are, for example, aluminum oxide, aluminum oxide hydrate, aluminum phosphates, borates and silicates. The slurries of the sparingly soluble aluminum compounds can be prepared by suspending finely particulate powders of these compounds in water with vigorous stirring. These slurries are advantageously obtained by precipitating the sparingly soluble aluminum compounds from aqueous aluminum salt solutions by means of bases.

Preferably, the catalysts according to the invention are prepared via a joint precipitation (mixed precipitation) of all of their components. For this purpose, an aqueous salt solution comprising the catalyst components is expediently admixed, at elevated temperature and with stirring, with an aqueous base—for example sodium carbonate, sodium hydroxide, potassium carbonate or potassium hydroxide—until the precipitation is complete. It is also possible to work with alkali metal-free bases such as ammonia, ammonium carbonate, ammonium hydrogencarbonate, ammonium carbamate, ammonium oxalate, ammonium malonate, urotropin, urea, etc. The type of salts used is generally not critical:

Since in this procedure what matters is primarily the solubility in water of the salts, one criterion is their good solubility in water required for producing the relatively highly concentrated salt solutions. It is considered to be self explanatory that when selecting the salts of the individual components, naturally only salts are selected with those anions which do not lead to disturbances, whether by causing undesired precipitations or by hindering or preventing precipitation as a result of complexation.

The precipitates obtained during these precipitation reactions are generally chemically nonuniform and consist inter alia of mixtures of the oxides, oxide hydrates, hydroxides, carbonates and insoluble and basic salts of the metals used. For the filterability of the precipitates, it may prove favorable if they are aged, i.e. if they are left to rest for some time after the precipitation, optionally at elevated temperature or while passing air through.

The precipitates obtained after these precipitation processes are further processed as usual to give the catalysts according to the invention. Firstly, the precipitates are washed. The duration of the washing process and the temperature and amount of wash water can be used to influence the content of alkali metal which has been introduced by the (mineral) base possibly used as precipitating agent. In general, extending the washing time or increasing the temperature of the wash water will reduce the content of alkali metal. After the washing, the precipitated material is generally dried at 80 to 200° C., preferably at 100 to 150° C., and then calcined. The calcination is generally carried out at temperatures between 300 and 800° C., preferably at 400 to 600° C., in particular at 420 to 550° C.

The catalysts according to the invention can also be produced by impregnating aluminum oxide ($Al_2O_3$), which is present, for example, in the form of powders or moldings, such as strands, tablets, beads or rings.

The aluminum oxide is used for example in the amorphous, gamma, theta and/or delta form, as aluminum oxohydroxide (boehmite), preferably in the amorphous form.

Moldings can be produced by customary methods.

The impregnation likewise takes place by customary methods, as described e.g. in A. B. Stiles, Catalyst Manufacture—Laboratory and Commercial Preparations, Marcel Dekker, New York (1983), by applying a corresponding metal salt solution in each case in one or more impregnation stages, using e.g. corresponding nitrates, acetates or chlorides as metal salts. After the impregnation, the mass is dried and optionally calcined.

The impregnation can take place by the so-called "incipient wetness" method, in which the aluminum oxide is wetted with the impregnation solution according to its water absorption capacity at most to the point of saturation. The impregnation can, however, also take place in supernatant solution. In the case of multistage impregnation methods, it is expedient to carry out drying and optionally calcination between individual impregnation steps. The multistage impregnation is to be used advantageously particularly when the aluminum oxide is to be supplied with a relatively large amount of metal.

To apply the metal components to the aluminum oxide, the impregnation can take place simultaneously with all metal salts or in any desired order of the individual metal salts in succession.

The catalysts prepared by impregnation are then dried and preferably also calcined, e.g. in the calcination temperature ranges already indicated above.

After the calcination, the catalyst is expediently conditioned whether by adjusting it to a certain particle size by grinding or by mixing it after it has been ground with shaping auxiliaries such as graphite or stearic acid, pressing by means of a press to give molded articles, e.g. tablets, and tempering. The tempering temperatures correspond here preferably to the temperatures during the calcination.

The catalysts prepared in this way comprise the catalytically active metals in the form of a mixture of their oxygen-containing compounds, i.e. in particular as oxides and mixed oxides.

The catalysts prepared e.g. as described above are stored and optionally handled as such. Prior to their use as catalysts, they are usually pre-reduced. However, they can also be used without pre-reduction, in which case they are then reduced under the conditions of the hydrogenating amination by the hydrogen present in the reactor.

For the pre-reduction, the catalysts are firstly subjected to a nitrogen/hydrogen atmosphere at preferably 150 to 200° C. over a period of e.g. 12 to 20 hours and then also treated in a hydrogen atmosphere for up to ca. 24 hours at preferably 200 to 400° C. During this pre-reduction, some of the oxygen-containing metal compounds present in the catalysts are reduced to the corresponding metals, meaning that these are present in the active form of the catalyst together with the various types of oxygen compounds.

The process according to the invention is preferably carried out continuously, in which case the catalyst is preferably arranged as a fixed bed in the reactor. In this connection, flow through the fixed catalyst bed from above and also from below is possible.

The ammonia is used in a 5- to 50-fold molar amount, preferably 11- to 45-fold molar amount, further preferably 13- to 40-fold molar amount, particularly 15- to 38-fold molar amount, in particular in a 17- to 36-fold molar amount, in a ≥20- to 36-fold molar amount, e.g. 22- to 35-fold molar amount, in each case based on the BDO used.

The ammonia can be used as aqueous solution, particularly as a 30 to 100% strength by weight aqueous solution, e.g. 50 to 90% strength by weight aqueous solution. It is preferably used without further solvent (compressed gas, purity particularly 95 to 100% strength by weight).

The starting material BDO can be used as solution, e.g. as aqueous solution, particularly as 75 to 95% strength by weight aqueous solution, or without solvent. Very particularly, it is used without solvent (preferred purity 95 to 100% strength by weight, particularly 98 to 100% strength by weight).

Preferably, an offgas amount of from 1 to 450 cubic meters (stp)/(m$^3$ of catalyst (bed volume)·h), in particular 2 to 200 cubic meters (stp)/(m$^3$ of catalyst (bed volume)·h), is processed. [cubic meters at standard temperature and pressure=volume converted to standard temperature and pressure conditions (20° C., 1 bar abs.)]. Catalyst volume data always refers to the bed volume.

The amination of the primary alcohol groups of the starting material BDO is carried out in the liquid phase. Preferably, the fixed bed process is in the liquid phase.

When working in the liquid phase, the starting materials (BDO, ammonia) are fed, preferably simultaneously, in liquid phase at pressures of from 16.0 to 22.0 MPa (160 to 220 bar), preferably 17.0 to 21.0 MPa, further preferably 18.0 to 20.0 MPa, further preferably 18.5 to 19.5 MPa, and temperatures of from 160 to 230° C., particularly 165 to 220° C., preferably 170 to 215° C., in particular 175 to 210° C., further particularly 180 to 200° C., further very particularly 180 to 195° C., e.g. 180 to 190° C., including hydrogen over the catalyst, which is usually located in a fixed-bed reactor heated preferably from the outside. Here, both a trickle mode and also a liquid-phase mode is possible. The trickle mode is preferred. The catalyst hourly space velocity is generally in the range from 0.1 to 0.7, preferably 0.15 to 0.6, particularly preferably 0.2 to 0.5, kg of BDO per liter of catalyst (bed volume) and per hour (BDO calculated as 100% strength by weight). Optionally, the starting materials can be diluted with a suitable solvent, such as water, tetrahydrofuran, dioxane, N-methylpyrrolidone or ethylene glycol dimethyl ether. It is expedient to heat the reactants even before they are introduced into the reaction vessel, preferably to the reaction temperature.

The reaction is carried out in the presence of 1.0 to 4.5% by weight of hydrogen, particularly in the presence of 1.2 to 4.5% by weight of hydrogen, further particularly in the presence of 1.5 to 4.0% by weight of hydrogen, very particularly in the presence of 2.0 to 4.0% by weight of hydrogen, further very particularly in the presence of 2.5 to 3.7% by weight of hydrogen, in each case based on the amount of BDO used.

The hydrogen is supplied to the reaction preferably in an amount in the range from 10 to 45 liters (stp) per mole of BDO, particularly 12 to 45 liters (stp) per mole of BDO, 15 to 40 liters (stp) per mole of BDO, 20 to 40 liters (stp) per mole of BDO, very particularly 25 to 37 liters (stp) per mole of BDO, (in each case measured at the reactor entrance). [liters (stp)=l (stp)=volume adjusted to standard temperature and pressure conditions (20° C., 1 bar abs.)].

(Note: 1.0 to 4.5% by weight of hydrogen, based on the amount of BDO used, corresponds to an amount of from 10 to 45 l (stp) of H$_2$ per mole of BDO).

The pressure in the reaction vessel which arises from the sum of the partial pressures of the ammonia, of the BDO and of the reaction products formed, and also optionally of the co-used solvent at the stated temperatures, is expediently increased to the desired reaction pressure by injecting hydrogen.

In the case of continuous operation in the liquid phase, the excess ammonia can be circulated together with the hydrogen.

If the catalyst is arranged as a fixed bed, it can be advantageous for the selectivity of the reaction to mix the catalyst moldings in the reactor with inert packings, to "dilute" them so to speak. The fraction of the packings in such catalyst preparations can be 20 to 80, particularly 30 to 60 and in particular 40 to 50, parts by volume.

The water of reaction formed in the course of the reaction (in each case one mole per mole of reacted alcohol group) generally does not have a disruptive effect on the degree of conversion, the rate of reaction, the selectivity and the service life of the catalyst and is therefore expediently only removed upon work-up of the reaction product, e.g. by distillation.

After the reaction discharge has expediently been decompressed, the excess hydrogen and the optionally present excess aminating agents are removed therefrom and the resulting crude reaction product is purified, e.g. by fractional rectification. Suitable work-up methods are described e.g. in EP 1 312 600 A and EP 1 312 599 A (both BASF AG). The excess ammonia and the hydrogen are advantageously returned again to the reaction zone. The same applies to any incompletely reacted BDO.

A work-up of the product of the reaction is preferably designed as follows
(steps i-vi):
(i) firstly unreacted ammonia is separated off overhead by distillation,
(ii) the process product pyrrolidine (I) is separated off overhead by distillation together with water and any by-products present having a lower boiling point than that of the process product I (low boilers), with any by-products present having a higher boiling point than that of process product I (high boilers) and any unreacted BDO (II) present remaining in the bottom,
(iii) the pyrrolidine (I) is dewatered in an extraction column,
(iv) residual amounts of water are separated off overhead from the resulting crude pyrrolidine by azeotropic distillation with pyrrolidine,
(v) the resulting pyrrolidine is further purified overhead by distillation, it being produced particularly in a purity of >97% by weight, very particularly 98 to 100% by weight.

By-products having a higher boiling point than that of the process product I (high boilers) are e.g. compounds with the following formulae:

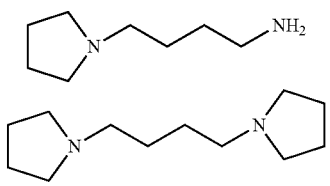

During the reaction of the process according to the invention, by-products which can arise are 4-amino-1-butanol with the formula III

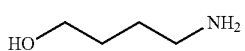 (III)

and also 1,4-diaminobutane with the formula IV

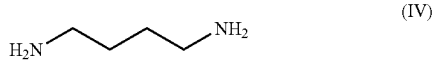 (IV)

which can both be reacted further in each case with ring closure (and release of $H_2O$ or $NH_3$, respectively) to give pyrrolidine (I).

Therefore, in particular by means of distillation,
(vi) from the bottom of step ii, any unreacted BDO (II) present and/or any 4-amino-1-butanol present as by-product with the formula III and/or any 1,4-diaminobutane present as by-product with the formula IV are separated off overhead and returned to the reaction.

Ammonia separated off in step i, particularly with a purity of from 90 to 99.9% by weight, further particularly 95 to 99.9% by weight, is preferably returned to the reaction, in which case, in one particular embodiment, some of the separated-off ammonia, particularly 1 to 30% by weight of the separated-off ammonia, further particularly 2 to 20% by weight of the separated-off ammonia, is removed from the system.

Water/pyrrolidine azeotrope separated off in step iv is preferably returned to the extraction column (step iii).

All pressure data refer to the absolute pressure.
All ppm data refer to the mass.

EXAMPLES

1. Preparation of catalyst A [=Example 4 in WO 2011/067199 A (BASF SE)]

An aqueous solution of nickel nitrate, cobalt nitrate, copper nitrate, aluminum nitrate and tin(II) chloride which comprised 3.9% by weight of Ni, 3.9% by weight of Co, 1.9% by weight of Cu, 5.5% by weight of $Al_2O_3$ and 0.5% by weight of Sn was precipitated simultaneously in a stirred vessel in a constant stream with a 20% strength by weight aqueous sodium carbonate solution at a temperature of 65-70° C. such that the pH of 5.7, measured using a glass electrode, was maintained. After the precipitation, air was blown in for 1 hour, then the pH of the solution was adjusted to 7.4 using sodium carbonate solution. The resultant suspension was filtered and the filtercake was washed with demineralized water until the electrical conductivity of the filtrate was ca. 20 mS. The filtercake was then dried in a drying cabinet at a temperature of 150° C. The hydroxide carbonate mixture obtained in this way was then calcined at a temperature of 500° C. for 4 hours. The catalyst mass was then mixed with 3% by weight of graphite and shaped to give tablets measuring 3×3 mm. The tablets obtained in this way are reduced in hydrogen at a temperature of 280-300° C. over at least 12 hours. The passivation of the reduced catalyst was carried out at room temperature in diluted air (air in N2 with an $O_2$ content of at most 5% by volume). The catalyst obtained in this way had the composition as shown in Table I below.

TABLE I

| Catalyst *) | Ni % | Co % | Cu % | Sn % | BET **) $m^2/g$ | Support |
|---|---|---|---|---|---|---|
| Catalyst A | 18.6 | 17.3 | 10.6 | 1.1 | 187 | $Al_2O_3$ |

*) Catalyst composition in % by weight; remainder up to 100% by weight is the support
**) ISO 9277: 1995

2. Reaction of BDO with Ammonia in Trickle Mode in a Continuously Operated Tubular Reactor (Shaft Reactor)

A heated tubular reactor with an internal diameter of 14 mm, a centrally mounted thermocouple and a total volume of 1000 ml was filled in the lower section with a layer of glass beads (250 ml), above these with 500 ml of the reduced catalyst A and finally the remaining section was filled again with glass beads. Before the reaction, the catalyst was activated at a maximum of 280° C. under hydrogen (25 l (stp)/h) [l (stp)=liters (stp)=volume adjusted to standard temperature and pressure conditions (20° C., 1 bar abs.)] at atmospheric pressure for 24 hours. A certain amount of BDO (99% strength by weight melt), ammonia and hydrogen, as given in Table II below, were metered through the reactor from top to bottom. The reactor was held at a temperature of ca. 178 to 184° C. (see table) and a total pressure of 190 bar. The reaction temperature was selected such that the BDO was completely converted. The mixture leaving the reactor was cooled and decompressed to atmospheric pressure. At various intervals, samples were taken from the reaction mixture and analyzed by means of gas chromatography. For this an "RTX-5 amine" GC column 30 m in length was used, with a temperature programme: 70° C./5 min., heat to 280° C. at a rate of 5° C./min., at 280° C./10 minutes.

The results of the experiments can be found in Table II below.

TABLE II

| Example | Temp. | HSV BDO | Molar ratio | Hydrogen (1) | (2) | (3) | (4) | (5) | BDO conversion | PYR Sel. | Feed number | Capacity |
|---|---|---|---|---|---|---|---|---|---|---|---|---|
| E1 | 183 | 0.26 | 20 | 13.5 | 27 | 79 | 0.4 | 2.71 | 100 | 70.3 | 180 | 146 |
| CE1a | 182 | 0.26 | 20 | 40.5 | 81 | 236 | 1.2 | 8.10 | 100 | 68.1 | 186 | 142 |
| CE1b | 178 | 0.26 | 20 | 90 | 180 | 526 | 2.6 | 18.06 | 100 | 58.0 | 218 | 120 |
| E2 | 183 | 0.26 | 25 | 13.5 | 27 | 79 | 0.4 | 2.71 | 100 | 74.0 | 171 | 154 |
| CE2 | 184 | 0.26 | 25 | 40.5 | 81 | 236 | 1.2 | 8.10 | 100 | 71.4 | 177 | 148 |
| E3 | 180 | 0.20 | 33 | 18 | 36 | 79 | 0.4 | 3.53 | 100 | 78.4 | 162 | 122 |
| CE3 | 180 | 0.20 | 33 | 54 | 108 | 236 | 1.2 | 10.54 | 100 | 75.5 | 168 | 118 |

Pressure: 190 bar
Examples: Examples according to the invention (E); Comparative Examples (CE)
Temp.: Temperature in the reactor in ° C.
HSV BDO: Hourly space velocity of butanediol in kg per liter of catalyst and per hour
MR: Molar ratio $NH_3$:BDO
Hydrogen: Given in 4 units: (1) liters (stp) per mole of alcohol function; (2) liters (stp) per mole of BDO; (3) cubic meters (stp) per cubic meter of catalyst and hour; (4) operating cubic meters (at operating pressure) per cubic meter of catalyst and hour; (5) % by weight based on the amount of BDO used
BDO conversion: Conversion of butanediol in %
PYR Sel.: Selectivity of pyrrolidine in mol %
Feed number: kg of butanediol per 100 kg of pyrrolidine
Capacity: kg of pyrrolidine per cubic meter of catalyst and hour The work-up can preferably take place by means of the following steps:

Performing the process with circulating gas (circulating-gas process): after passing through the reactor, the mixture is cooled and the gas phase is separated off from the liquid phase. The gas phase, which consists primarily of hydrogen and in part of ammonia, is returned to the reactor as circulating gas. Consumption and loss of hydrogen is compensated with fresh $H_2$ gas in order to keep the pressure in the reactor constant.

When performing the process without circulating gas, the fresh $H_2$ gas is fed into the reactor in a straight pass and disposed of after the high-pressure separator.

In a column, the ammonia ($NH_3$) is separated off from the liquid discharge and preferably returned to the reactor. Optionally, some of the ammonia is bled off from the top of the column. The liquid discharge is then worked up:

In a first distillation column, high boilers (relatively high boiling secondary components) are separated off in the bottom and pyrrolidine is drawn off overhead together with water and other low boilers.

In an extraction column, dewatering is carried out with 50% strength by weight sodium hydroxide solution.

In a second distillation column, the residual water in the pyrrolidine is separated off overhead as an azeotrope with pyrrolidine and preferably returned to the extraction column.

In a third distillation column, pure pyrrolidine, preferably in a purity of 98 to 100% by weight, is distilled off.

The invention claimed is:

1. A process for preparing pyrrolidine of the formula I

(I)

comprising reacting 1,4-butanediol (BDO) of the formula II

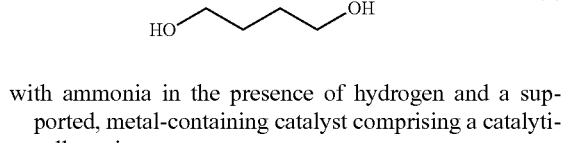
(II)

with ammonia in the presence of hydrogen and a supported, metal-containing catalyst comprising a catalytically active mass,
wherein the catalytically active mass of the catalyst, prior to its reduction with hydrogen, comprises oxygen-containing compounds of aluminum, copper, nickel and cobalt and from 0.2 to 5.0% by weight of oxygen-containing compounds of tin, calculated as SnO,
wherein the reacting step is carried out in a liquid phase at an absolute pressure from 160 to 220 bar, at a temperature from 160 to 230° C., in the presence of 1.0 to 4.5% by weight of hydrogen based on the amount of BDO, and the ammonia is in a molar ratio of ammonia to BDO ranges from 5 to 50.

2. The process according to claim 1, wherein the catalytically active mass of the catalyst, prior to its reduction with hydrogen, comprises from 0.4 to 4.0% by weight of oxygen-containing compounds of tin, calculated as SnO.

3. The process according to claim 1, wherein the catalytically active mass of the catalyst, prior to its reduction with hydrogen, comprises from 0.6 to 3.0% by weight of oxygen-containing compounds of tin, calculated as SnO.

4. The process according to claim 1, wherein the catalytically active mass of the catalyst, prior to its reduction with hydrogen, comprises from 5.0 to 35% by weight of oxygen-containing compounds of cobalt, calculated as CoO.

5. The process according to claim 1, wherein the catalytically active mass of the catalyst, prior to its reduction with hydrogen, comprises from 10 to 30% by weight of oxygen-containing compounds of cobalt, calculated as CoO.

6. The process according to claim 1, wherein the catalytically active mass of the catalyst, prior to its reduction with hydrogen, comprises from
15 to 80% by weight of oxygen-containing compounds of aluminum, calculated as $Al_2O_3$,
1.0 to 20% by weight of oxygen-containing compounds of copper, calculated as CuO, and
5.0 to 35% by weight of oxygen-containing compounds of nickel, calculated as NiO.

7. The process according to claim 1, wherein the catalytically active mass of the catalyst, prior to its reduction with hydrogen, comprises from
   30 to 70% by weight of oxygen-containing compounds of aluminum, calculated as $Al_2O_3$,
   2.0 to 18% by weight of oxygen-containing compounds of copper, calculated as CuO, and
   10 to 30% by weight of oxygen-containing compounds of nickel, calculated as NiO.

8. The process according to claim 1, wherein the molar ratio of nickel to copper in the catalyst is greater than 1.

9. The process according to claim 1, wherein the catalytically active mass of the catalyst comprises no rhenium and/or ruthenium.

10. The process according to claim 1, wherein the catalytically active mass of the catalyst comprises no iron and/or zinc.

11. The process according to claim 1, wherein the catalytically active mass of the catalyst comprises no oxygen-containing compounds of silicon and/or of zirconium and/or of titanium.

12. The process according to claim 1, wherein the reaction is carried out at a temperature from 165 to 220° C.

13. The process according to claim 1, wherein the reaction is carried out at an absolute pressure from 170 to 210 bar.

14. The process according to claim 1, wherein the molar ratio of ammonia is an 11- to 45-fold molar amount, based on the BDO used.

15. The process according to claim 1, wherein the reaction is carried out in the presence of from 1.2 to 4.5% by weight of hydrogen, based on the amount of BDO.

16. The process according to claim 1, wherein the catalyst is arranged as a fixed bed in a reactor.

17. The process according to claim 1, wherein the reaction takes place in a trickle mode.

18. The process according to claim 1, wherein the process is carried out continuously.

19. The process according claim 18, wherein the reaction takes place in a tubular reactor.

20. The process according to claim 18, wherein the reaction takes place in a circulating-gas mode.

21. The process according to claim 1, wherein the BDO is solvent-free.

22. The process according to claim 1, wherein the ammonia is an aqueous solution.

23. The process according to claim 1, wherein the reaction is carried out at a catalyst hourly space velocity from 0.1 to 0.7 kg of BDO/(lcat.·h).

24. The process according to claim 1, further comprising working up the process product pyrrolidine by the following steps:
   (i) separating off unreacted ammonia overhead by distillation,
   (ii) separating off the process product pyrrolidine overhead by distillation together with water and any by-products present having a lower boiling point than that of the process product pyrrolidine, wherein any by-products present having a higher boiling point than that of the process product pyrrolidine and any unreacted BDO present remain in the bottom,
   (iii) dewatering the pyrrolidine of the formula I in an extraction column,
   (iv) separating off overhead residual amounts of water from the resulting crude pyrrolidine formed by step (iii) by azeotropic distillation with pyrrolidine, and
   (v) purifying further the resulting pyrrolidine formed by step (iv) overhead by distillation.

25. The process according to claim 24, further comprising
   (vi) separating off overhead and returning to the reaction by distillation, from the bottom of step (ii), any unreacted BDO present and/or any 4-amino-1-butanol present as by-product with the formula III

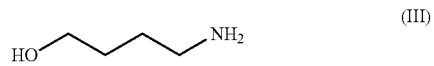

and/or any 1,4-diaminobutane present as by-product with the formula IV

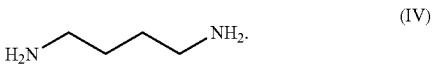

26. The process according to claim 24, further comprising returning the ammonia separated off in step (i) to the reaction, wherein the ammonia separated off in step (i) has a purity of from 90 to 99.9% by weight.

27. The process according to claim 24, wherein the water with pyrrolidine separated off in step (iv) is returned to the extraction column.

* * * * *